United States Patent [19]
Blenkle

[11] Patent Number: 5,220,362
[45] Date of Patent: Jun. 15, 1993

[54] OPHTHALMIC LIGHTING APPARATUS

[75] Inventor: Paul E. Blenkle, Palatine, Ill.

[73] Assignee: Woodlyn Inc., Arlington Heights, Ill.

[21] Appl. No.: 785,487

[22] Filed: Oct. 31, 1991

[51] Int. Cl.⁵ .............................................. A61B 3/02
[52] U.S. Cl. ................................... 351/235; 351/239; 351/243
[58] Field of Search ............... 351/203, 211, 235, 237, 351/239, 243

[56] References Cited

U.S. PATENT DOCUMENTS 4,222,639  9/1980  Sheedy ................................ 351/243

OTHER PUBLICATIONS

P. 54 from 1989–1990 Frames Product Guide, Ophthalmic Instrument & Equipment Catalog.
P. 181 from 1987 WCO Ophthalmic & Surgical Instrument Catalog.
P. 54 from 1961 Opthalmic Instrument Handbook Catalog.
P. 56 from 1961 Ophthalmic Instrument Handbook Catalog.
P. 106 from 1961 Ophthalmic Instrument Handbook Catalog.

*Primary Examiner*—Rodney B. Bovernick
*Assistant Examiner*—Hung Xuan Dang
*Attorney, Agent, or Firm*—Dick and Harris

[57] ABSTRACT

An ophthalmic lighting apparatus for operable attachment to ophthalmic articles, such as ophthalmic refractors, which articles are capable of supporting and deploying a protruding reading card rod, a reading card holder and accordingly a reading card during an ophthalmic examination. An illumination member is operably attached to one or more of the components of the reading card assembly for providing a controlled and standardized amount of light to the reading card. A position sensitive switch is interposed between a power source and the illumination member for automatically switching a light source upon movement of the reading card rod from a vertically protruding pre-ophthalmic examination position to a substantially horizontal protruding ophthalmic examination position.

13 Claims, 3 Drawing Sheets

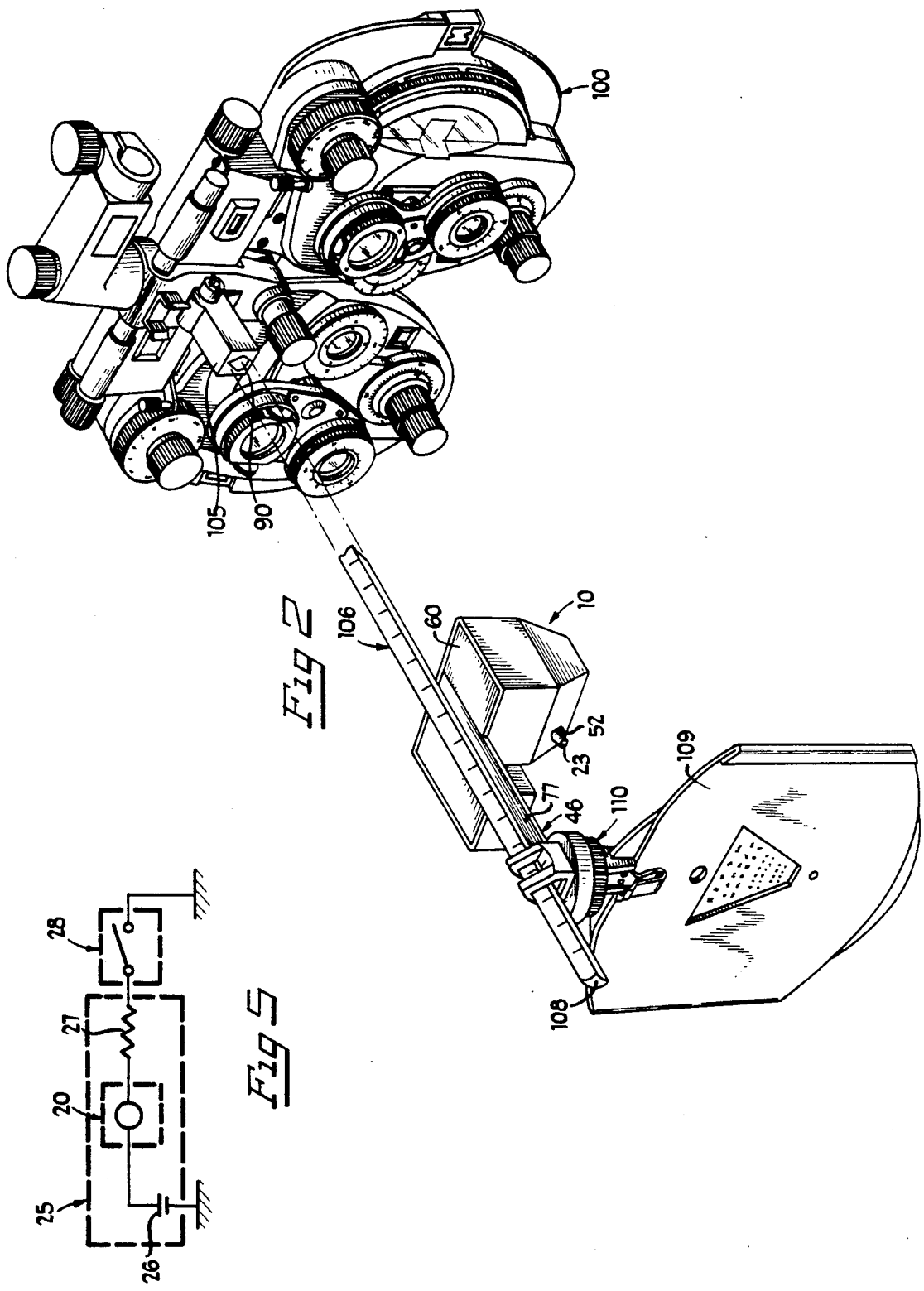

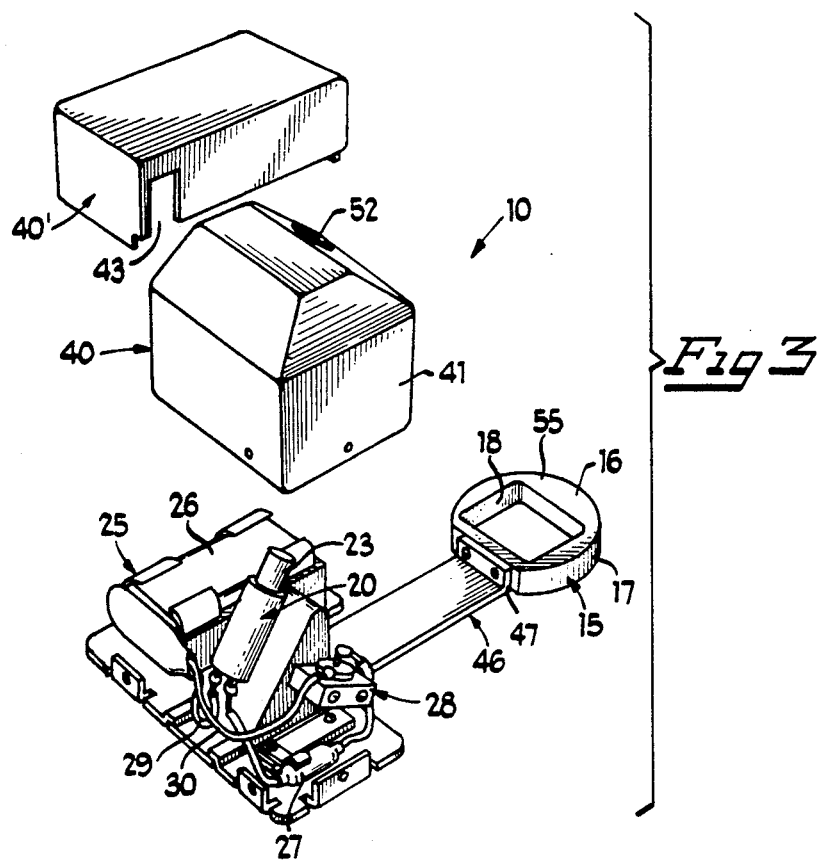
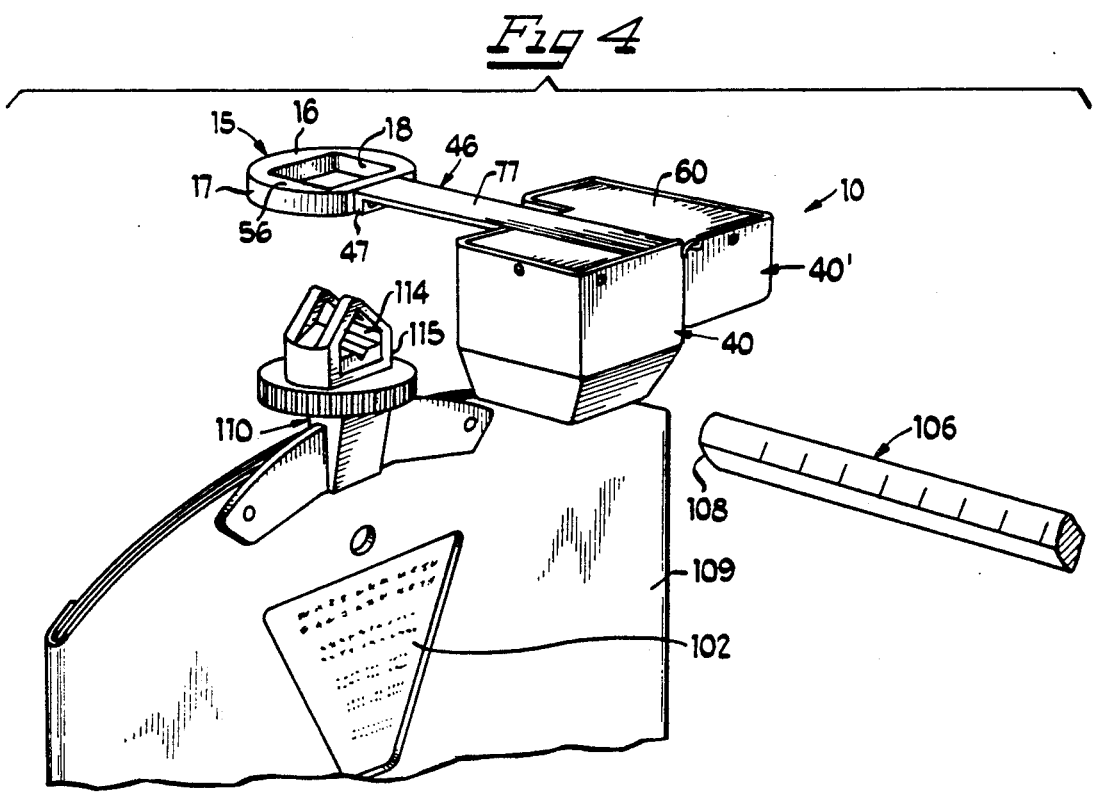

OPHTHALMIC LIGHTING APPARATUS

BACKGROUND OF THE INVENTION

The present invention relates to ophthalmic examination equipment and, more particularly, to an ophthalmic lighting apparatus for operable attachment to an ophthalmic article, such as an ophthalmic refractor, of the type which has an attachment element capable of supporting a reading card rod, and accordingly a reading card holder and reading card, so as to provide controlled and standardized illumination of at least a portion of the reading card during the ophthalmic examination.

Lighting devices used for illuminating reading cards of the type operably attached to ophthalmic articles such as ophthalmic refractors have been known in the art for many years. Many of such lighting devices are typically in the form of conventional multi-positionable lamps independently positioned and physically isolated from the ophthalmic article itself, which ophthalmic refractor, for example, utilizes a reading card assembly. The position and illumination of such independent light sources are, unfortunately, rarely maintained at a specific recommended illumination level, much less a predetermined, calibrated, distance away from the reading card during the actual ophthalmic examination. Accordingly, one of several problems associated with the use of such conventional independent lamps, is that the brightness of the light projected onto the reading card typically exceeds the ten to twenty foot candle illumination protocol recommended for an ophthalmic reading test. Accordingly, the results of the reading test may often be inconsistent, and in many cases, in error—with some patients complaining that their reading glasses "worked better" during examination than in use; due to over illumination of the reading test card. In addition, inasmuch as the lamps are not maintained in a predetermined, calibrated, orientation with respect to the reading card, the intensity of light projected onto the reading card may vary from examination to examination, with the wrong intensity of light otherwise recommended for such an examination being projected onto the reading card—thereby potentially resulting in an inaccurate diagnosis by the examiner.

It is accordingly not uncommon for an optometrist or ophthalmologist to prescribe corrective lenses to a patient, for reading, based upon the results of a reading examination given in association with a non-calibrated, non protocol-conforming conventional light projector, only to later find out that such lenses do not adequately correct the patients vision when he or she is attempting to read in a "real world" environment. Furthermore, inasmuch as many conventional style lamps are multi-positionable, and, accordingly, constantly re-adjusted (i.e. by swinging the lamp into proximate position for the examination, followed by making further manual adjustments thereto followed by raising the lamp and swinging it out of the way after the examination) breakage and/or other forms of malfunction of the lamp are not uncommon.

It is thus an object of the present invention to provide an ophthalmic lighting apparatus which is maintained at a predetermined, calibrated, position away from the reading card, so as to ensure that the industry recommended amount of light is being projected onto the reading card during every ophthalmic examination given.

It is also an object of the present invention to provide an ophthalmic lighting apparatus which is operably attached to a portion of an ophthalmic article, such as a reading card holder attached to an ophthalmic refractor, so that constant reorientation of the lighting apparatus, with respect to the reading card, is not required.

It is still further an object of the present invention to provide an ophthalmic lighting apparatus which includes a position sensitive switch which automatically results in the projection of light when the apparatus is in an ophthalmic examination position and automatically shuts of the light when the lighting apparatus is in a pre-ophthalmic examination position—while isolating wall current electrical conductors from contact with the metal refractor.

These and other objects of the present invention will become apparent in light of the present specification and drawings.

SUMMARY OF THE INVENTION

The present invention comprises an ophthalmic lighting apparatus for operable attachment to ophthalmic articles, such as ophthalmic refractors, which articles are of the type having a reading card assembly including a reading card rod attachment element capable of operably supporting a protruding reading card rod, along with a reading card holder and a reading card supported by the reading card holder in front of the ophthalmic article for use in association with ophthalmic examinations; for providing controlled and standardized illumination to at least a portion of the reading card during the ophthalmic examination.

The ophthalmic lighting apparatus includes apparatus attachment means for operably securing the ophthalmic lighting apparatus to at least a portion of said reading card assembly. Illumination means are operably attachable along the reading card rod in a facilitated manner for projecting a desired, calibrated amount of light towards and onto the reading card during the ophthalmic examination to, in turn, obviate the need to utilize externally positioned non-calibrated illumination devices.

Power means are operably attached to the illumination means for providing electricity to the illumination means, to, in turn, enable the projection of the desired amount of light toward and onto the reading card. In addition, switch means are operably interposed between the power means and the illumination means for alternatively opening and closing the flow of electricity from the power means to the illumination means.

A housing means has an exterior surface and an interior surface defining a component protection region which operably surrounds and shields at least a portion of one or more of the power means, the illumination means and the switch means within the component protection region. In addition, positioning means are operably interposed between the illumination means and reading card, for operably maintaining the illumination means at a desired distance away from the reading card.

In the preferred embodiment of the invention, the switching means comprises a position sensitive switch. This switch automatically opens the flow of electricity from the power means to the illumination means when the reading card rod, and, in turn, the reading card, are in an extended deployed, ophthalmic examination position. Conversely, the position sensitive switch closes the flow of electricity from the power means to the illumination means when the reading card rod, reading card holder and reading card are in a pre-ophthalmic examination position. The position sensitive switch itself preferably comprises a mercury switch. In this embodiment, the switch will be in an open-flow position when the reading card rod is in a substantially horizontal protruding examination position, and closed to power flow when the reading card rod is raised to a substantially vertical, protruding pre-examination position—thereby preventing the flow of electricity to the illumination means.

In a preferred embodiment of the invention, the power means includes a battery for providing electricity to the illumination means so as to preclude the need to attach the ophthalmic lighting device to conventional socket current during use thereof, thereby insulating a typically metallic refractor from direct contact with dangerous, high current 110 volt conductor wires. The low current battery power means further includes electricity conduit means operably connected to the switching means and the illumination means.

In the preferred embodiment of the invention, the illumination means comprises a light bulb which is operably exposed to the reading card for illuminating the reading card during the ophthalmic examination through the projection of light thereupon. The light bulb may further include magnifying lens means which are operably positioned adjacent the light bulb. The magnifying lens means are positioned in exposed relationship to the reading card for intensifying light projected from the light bulb toward and onto the reading card. It is also contemplated that the illumination means may further include light diffusion means which are operably associated with the light bulb and/or the magnifying lens means. The light diffusion mean are positioned in exposed relationship to the reading card for operable directing and concentrating the light emitted from the light bulb and, alternatively, the magnifying lens means toward and onto the reading card. The light diffusion means may comprise a fiber optic element.

In another embodiment of the invention, the apparatus attachment means is removably secured to at least a portion of the ophthalmic article. This bracket may be slidably engageable over at least a portion of a conventional reading card holder for standardized removable securement thereto.

In the preferred embodiment of the invention, the illumination means projects an intensity of light of between ten and twenty foot candles onto the reading card when the switch means, the reading card rod, reading card holder and reading card, are in the substantially horizontal ophthalmic examination position. The intensity of projected light is a function of the power means, the illumination means and the distance at which the illumination means is maintained away from the reading card by the positioning means.

BRIEF DESCRIPTION OF THE DRAWINGS

FIG. 2 of the drawings is a front perspective view of the ophthalmic lighting apparatus in its intended environment, and more specifically, operably attached to a conventional reading card assembly, showing, in particular, the predetermined calibrated distance between the illumination means and the reading card, as well as showing the substantially horizontal protruding orientation of the reading card rod, and, accordingly, the ophthalmic lighting apparatus in an ophthalmic examination position;

FIG. 3 of the drawings is an exploded perspective view of the ophthalmic lighting apparatus, showing, in particular, the housing means, the power means, the illumination means, the switching means, the positioning means and the bracket used for attachment to the conventional reading card holder;

FIG. 4 of the drawings is an exploded perspective view of the ophthalmic lighting apparatus prior to securing the positioning means to the reading card rod acceptance bracket of the conventional card holder, and prior to insertion of the reading card rod through the reading card rod receiving slot after the ophthalmic lighting apparatus has been properly engaged thereon; and FIG. 5 of the drawings is a schematic diagram of the power means, illumination means and switching means circuit.

DETAILED DESCRIPTION OF THE DRAWINGS

Figure 1:
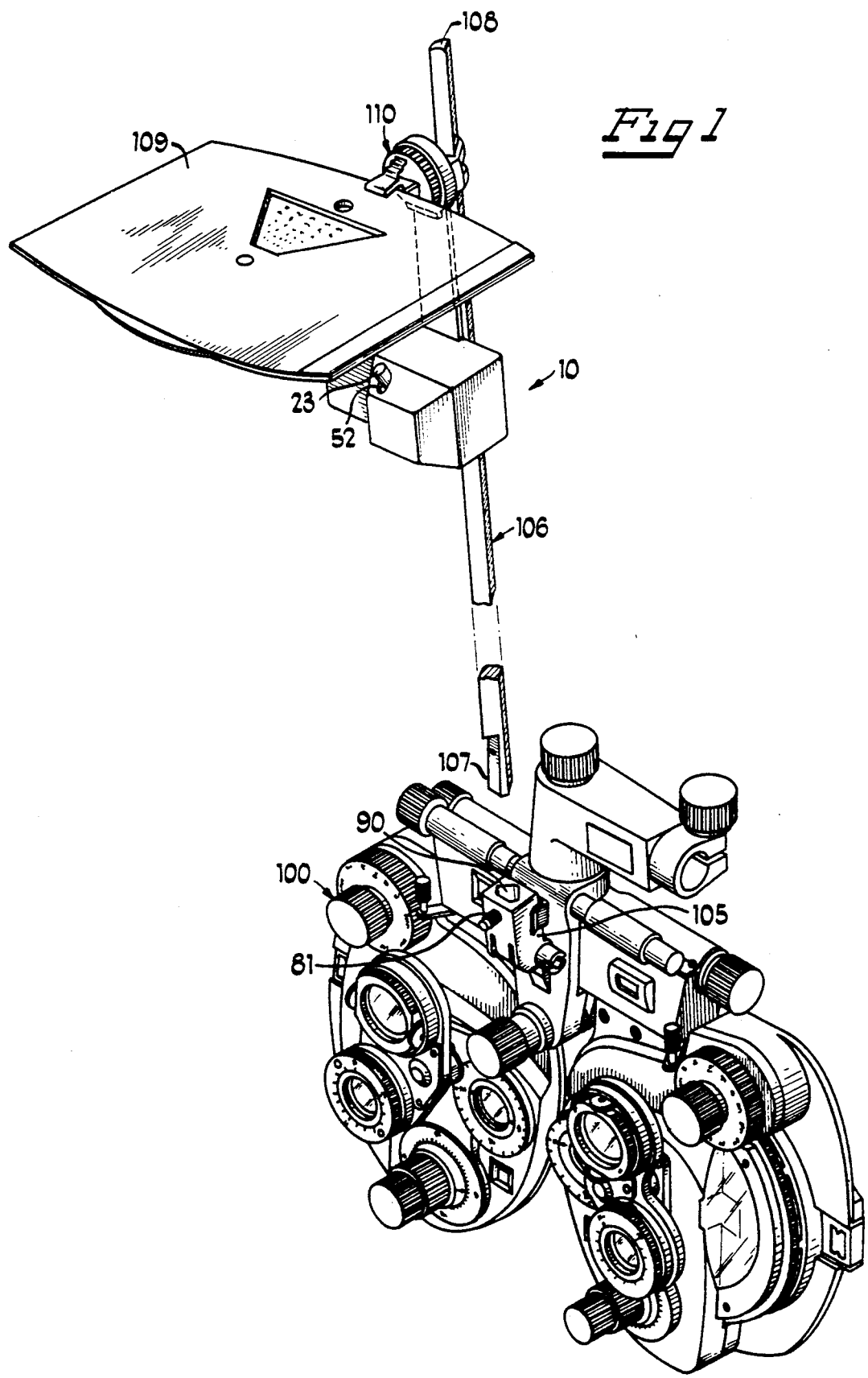
FIG. 1 of the drawings is a front perspective view of the ophthalmic lighting apparatus in its intended environment, and more specifically, operably attached to a conventional reading card assembly, showing, in particular, the predetermined calibrated distance between the illumination means and the reading card, as well as showing the substantially vertically protruding orientation of the reading card rod, and, accordingly, the ophthalmic lighting apparatus in a pre-ophthalmic examination position.

While this invention is susceptible of embodiment in many different forms, there is shown in the drawings and will herein be described in detail, one specific embodiment with the understanding that the present disclosure is to be considered as an exemplification of the principles of the invention and is not intended to limit the invention to the embodiment illustrated.

Ophthalmic lighting apparatus 10 is shown in FIG. 1 and FIG. 2 in its intended environment, and specifically, as integrally, yet removably attached to a conventional reading card assembly which comprises a reading card 109, reading card holder 110 and a reading card rod 106 for use with a conventional ophthalmic article, such as ophthalmic refractor 100. As shown, reading card holder 110, (and accordingly, ophthalmic lighting apparatus 10) is operably secured to ophthalmic refractor 100 through cooperation with reading card rod 106. Reading card rod 106 has a first end 107 and a second end 108. First end 107 of reading card rod 106 is operably inserted within slot 90 of conventional reading rod attachment element 105 which is pivotally attached to ophthalmic refractor 100. Restraint screw 81 fixedly restrains rod 106 within slot 90. Second end 108 of reading rod 106 is operably inserted and secured within reading card rod receiving slot 114 of reading card rod acceptance bracket 115 on reading card holder 110, as shown more fully in FIG. 4.

Ophthalmic lighting apparatus 10 is shown in FIG. 3 as comprising housing means 40 and 40', illumination means 20, power means 25, switch means 28, positioning means 46 and apparatus attachment means 15 which is integrally connected to first end 47 of positioning means 46. Illumination means 20, which serves to illuminate a relevant portion of reading card 109 (FIG. 4), may include a light bulb and magnifying lens (not shown) as well as fiber optic element 23. Fiber optic 23 is operably positioned above the bulb/magnifying lens assembly within illumination means 20 so that the light being emitted from the light bulb is first magnified and then transmitted through the fiber optic where it is then diffused and directed to and concentrated on, a relevant portion of reading card 109 (FIG. 4). Although the bulb/magnifying assembly is not shown, a commercially suitable assembly, such as a light bulb capable of drawing three volts of electricity at 0.006 amps of current, coupled with a magnifying lens capable, for example, of twenty times magnification of the light projected from the bulb, can be used. An example of such a light bulb/magnifying lens combination is commercially available from Hamai Corporation under its catalog number LNS-BP4-20K. In addition, any suitable plastic fiber optic element may be utilized.

Power means 25, which serves to electrically power illumination means 20, is shown in FIG. 3 and FIG. 5 as including battery 26 and resistor 27. Battery 26 is operably connected to illumination means 20, resistor 27, as well as switch means 28, by electrical conduit, such as electrical conduits 29 and 30. Use of a battery, as opposed to common current from a typical electrical outlet is desired inasmuch as such a self-contained power source substantially reduces the risk of electrical shock which could otherwise occur from a short in the electrical connection from a standard 110 volt outlet—especially inasmuch as the patient being examined usually has his or her face pressed against a portion of the metal casing of ophthalmic refractor 100. Although battery 26 is contemplated to be a readily available 9 volt transistor radio battery, and, resistor 27 is contemplated to be a commercially available resistor having approximately ten ohms of resistance, many other types of batteries and resistor combinations are also contemplated—provided that such a combination enables the desired amount of light to be projected onto reading card 109 from illumination means 20 during the ophthalmic examination.

Switch 28, which is interposed between battery 26 and illumination means 20 (FIG. 3 and FIG. 5), serves to allow, or preclude the flow of electricity from battery 26 to illumination means 20. It is preferred that switch 28 comprise a position sensitive switch, such as a mercury switch, so as to automatically open and close the flow of electricity to illumination means 20, depending upon the orientation of ophthalmic lighting apparatus 10. Indeed, when ophthalmic lighting apparatus 10, and accordingly reading card rod 106, are in a substantially vertical protruding orientation, as shown in FIG. 1, then the apparatus will be in its pre-ophthalmic examination position. Accordingly, when in such a position, switch 28 will preclude the flow of electricity to illumination means 20. Conversely, when ophthalmic lighting device 10, and accordingly reading card rod 106, are in a substantially horizontal protruding orientation, as shown in FIG. 2, then the apparatus will be in an ophthalmic examination position, so that switch means 28 will automatically allow the flow of electricity to illumination means 20. Simply re-orientating the apparatus from the pre-examination position to the examination position will automatically cause switch means 28 to permit electric power to flow to illumination means 20. Such a position sensitive switch is available from Micro-Dynamic Corporation under its catalog number 5-2-10—although any other suitable position sensitive switch can be used for such automatic "on" and "off" switching.

Housing means 40 and 40', as shown in FIG. 3, each include an exterior surface, such as exterior surface 41, and an interior surface (not shown) which defines a component protection region (also not shown). In addition, housing means 40' which enshrouds battery 26, includes conduit aperture 43 which facilitates unobstructed passage of electrical conduit, such as connectors 29 and 30 from battery 26 to illumination means 20, as well as to switching means 28. The housing means serves to protect the inner componentry, and more specifically, the illumination means 20, power means 25, and switch means 28 from potential damage which could result from exposure to the external contact, while serving to preclude injury which could result from even nominal electrical shock. Furthermore, housing means 40 which substantially covers illumination means 20, switching means 28 and resistor 27, additionally includes an illumination projection portal 52, as shown more fully in FIG. 1 and FIG. 2. This illumination projection portal enables at least a portion of fiber optic 23 to extend past exterior surface 41 of housing means 40, so as to facilitate the unobstructed projection of the necessary amount of light from illumination means 20 onto reading surface 102 (FIG. 4) of reading card 109.

Positioning means 46, as shown in FIG. 3 and FIG. 4, includes first end 47 and second end 48. Second end 48 is operably attached to support member 60, which supports illumination means 20, power means 25 and switch means 28, while first end 47 is operably attached to apparatus attachment means 15 which is removably secured to reading card holder 110—so as to maintain illumination means 20 at a predetermined, calibrated, distance away from the relevant portion of reading card 109 (FIG. 2). Accordingly, such maintained, interposed orientation of positioning means 46 ensures that the amount of light being projected from illumination means 20 onto reading card 109, can be set to a desired constant, even if adjustable, examination after examination. Although any desired amount of illumination can be achieved, it is preferable that positioning means 46 have a length which, along with the foot candle capacity of the illumination means, enables the projection of light onto reading card 109 to be between the recommended industry standard of ten to twenty foot candles.

Apparatus attachment means 15, which enables removable securement of apparatus 10 to reading card holder 110, comprises bracket 16 having top surface 55, bottom surface 56, outer periphery 17 and an inner shaped periphery 18. As can be seen, inner periphery 18 has a configuration substantially similar to the outer periphery of standardized reading card rod acceptance bracket 115, so as to enable use of apparatus 10 as a readily attachable accessory on existing card holder elements. Accordingly, bracket 16 will operably fit over and around reading card rod acceptance bracket 115 with very little free play. Additional securement of the apparatus to the card holder may be obtained, by utilization of commercially available fastening members, such as screws, wing nuts, allan screws or thumb screws in attachment means 15. After bracket 16, and accordingly ophthalmic lighting apparatus 10, have been operably attached to card holder 110, reading card rod 106 is slid into slot 114 of reading card rod acceptance bracket 115, of card holder 110, so as to facilitate operable cooperation with ophthalmic refractor 100 during an examination, or, pre-examination orientation. Once properly inserted, reading card rod 106 will be positioned adjacent to bottom side 77 of apparatus 10 to further provide stability thereto. In addition, inasmuch as the transverse cross-sectional thickness of bracket 16 does not extend above the base of the reading card rod receiving slot 114 (FIG. 4) when bracket 16 is operably attached to reading card rod acceptance bracket 115, reading card rod 106 will be able to be inserted within acceptance slot 114 without any obstruction.

The foregoing description and drawings merely explain and illustrate the invention and the invention is not limited thereto except insofar as the appended claims are so limited, as those skilled in the art who have the disclosure before them will be able to make modifications and variations therein without departing from the scope of the invention.

What is claimed is:

1. An ophthalmic lighting apparatus for operable attachment to ophthalmic articles, such as ophthalmic refractors, which articles are of the type having a reading card assembly including a reading card rod attachment element capable of operably supporting a protruding reading card rod, along with a reading card holder and a reading card supported by said reading card holder, in front of said ophthalmic article for use in ophthalmic examinations, wherein said reading card has a front surface capable of exposure to said ophthalmic article, said ophthalmic lighting apparatus providing controlled and standardized illumination to at least a portion of said reading card during said ophthalmic examination, said ophthalmic lighting apparatus comprising:

apparatus attachment means for operably securing said ophthalmic lighting apparatus to at least a portion of said reading card assembly;

illumination means operably positioned along said reading card rod between said front surface of said reading card and said ophthalmic article for projecting a desired, calibrated amount of light toward and onto said front surface of said reading card during said ophthalmic examination to, in turn, obviate the need to utilize externally positioned non-calibrated illumination devices;

power means operably attached to said illumination means for electrically illuminating said illumination means, to, in turn, enable the projection of said desired amount of light toward and onto said reading card;

switch means operably interposed between said power means and said illumination means for alternatively opening and closing the flow of electricity from said power means to said illumination means;

housing means having an exterior surface and an interior surface defining a component protection region for operably surrounding and shielding at least a portion of one or more of said power means, said illumination means and said switch means within said component protection region; and positioning means operably interposed between said illumination means and, said front surface of said reading card for operably maintaining said illumination means at a desired distance from said front surface of said reading card.

2. The invention according to claim 1 in which said power means includes a battery for providing electricity to said illumination means so as to preclude the need to attach said ophthalmic lighting apparatus to conventional socket current during use thereof, said power means further including electricity conduit means operably connected between said switching means and said illumination means.

3. The invention according to claim 1 in which said illumination means comprises a light bulb operably exposed to said reading card for illuminating said reading card during said ophthalmic examination through the projection of light thereupon.

4. The invention according to claim 3 in which said light bulb further includes magnifying lens means operably associated with said light bulb, said magnifying lens means being positioned to intensify said light projecting from said light bulb toward and onto said reading card.

5. The invention according to claim 4 in which said illumination means further includes light diffusion means operably associated with one or more of said light bulb and said magnifying lens means, said light diffusion means being positioned in exposed relationship to said reading card for operably directing and concentrating s id light projected from said light bulb and magnifying lens means toward and onto said reading card, said light diffusion means comprising a fiber optic element.

6. The invention according to claim 3 in which said illumination means further includes light diffusion means operably associated with said light bulb, said light diffusion means being positioned in exposed relationship to said reading card for operably directing and concentrating said light projected from said light bulb toward and onto said reading card, said light diffusion means comprising a fiber optic element.

7. The invention according to claim 1 in which said apparatus attachment means comprises a bracket slidably engageable over at least a portion of a conventional reading card holder for standardized removable securement thereto.

8. The invention according to claim 1 in which said reading card rod, reading card holder and reading card are deployable between a substantially vertically oriented pre-ophthalmic examination position and a substantially horizontal ophthalmic examination position wherein at least a portion of said reading card is in viewable alignment with said ophthalmic article;

said switch means including a position sensitive switch;

said position sensitive switch comprising means for automatically opening said flow of electricity from said power means to said illumination means when said reading card rod, and, in turn, said reading card holder are in said ophthalmic examination position, and, said position sensitive switch including means for automatically closing the flow of electricity from said power means to said illumination means when said reading card rod, and, in turn, said reading card holder and reading card are in said preophthalmic examination position.

9. The invention according to claim 8 in which said position sensitive switch comprises a mercury switch.

10. The invention according to claim 8 in which said illumination means projects an intensity of light of between ten and twenty foot candles onto said reading card when said switch means, said reading card rod and accordingly said reading card holder and reading card, are in said ophthalmic examination position, said intensity of projected light being a function of said power means, said illumination means and the distance at which said illumination means is maintained away from said reading card by said positioning means.

11. An ophthalmic lighting apparatus for operable attachment to ophthalmic articles, such as ophthalmic refractors, which articles are of the type having a reading card assembly including a reading card rod attachment element capable of operably supporting a protruding reading card rod, along with a reading card holder and a reading card supported by said reading card holder, in front of said ophthalmic article for use in ophthalmic examinations, said ophthalmic lighting apparatus providing controlled and standardized illumination to at least a portion of said reading card during said ophthalmic examination, said ophthalmic lighting apparatus comprising:

apparatus attachment means for operably securing said ophthalmic lighting apparatus to at least a portion of said reading card assembly;

illumination means operably attachable along said reading card rod in a facilitated manner for projecting a desired, calibrated amount of light toward and onto said reading card during said ophthalmic examination to, in turn, obviate the need to utilize externally positioned non-calibrated illumination devices;

power means operably attached to said illumination means for electrically illuminating said illumination means, to, in turn, enable the projection of said desired amount of light toward and onto said reading card;

switch means operably interposed between said power means and said illumination means for alternatively opening and closing the flow of electricity from said power means to said illumination means;

housing means having an exterior surface of an interior surface defining a component protection region for operably surrounding and shielding at least a portion of one or more of said power means, said illumination means and said switch means within said component protection region; and positioning means operably interposed between said illumination means and, said reading card for operably maintaining said illumination means at a desired distance from said reading card, said reading card rod, reading card holder and reading card being deployable between a substantially vertically oriented pre-ophthalmic examination position and a substantially horizontal ophthalmic examination position wherein at least a portion of said reading card is in viewable alignment with said ophthalmic article;

said switch means including a position sensitive switch;

said position sensitive switch comprising means for automatically opening said flow of electricity from said power means to said illumination means when said reading card rod, and, in turn, said reading card holder and reading card are in said ophthalmic examination position;

said position sensitive switch including means for automatically closing the flow of electricity from said power means to said illumination means when said reading card rod, and, in turn, said reading card holder and reading card are in said pre-ophthalmic examination position.

12. The invention according to claim 11 in which said position sensitive switch comprises a mercury switch.

13. The invention according to claim 12 in which said illumination means projects an intensity of light of between ten and twenty foot candles onto said reading card when said switch means, said reading card rod and accordingly said reading card holder and reading card, are in said ophthalmic examination position, said intensity of projected light being a function of said power means, said illumination means and the distance at which said illumination means is maintained away from said reading card by said positioning means.

* * * * *

UNITED STATES PATENT AND TRADEMARK OFFICE
CERTIFICATE OF CORRECTION

PATENT NO. : 5,220,362
DATED : June 15, 1993
INVENTOR(S) : Paul E. Blenkle

It is certified that error appears in the above-indentified patent and that said Letters Patent is hereby corrected as shown below:

Col. 2, line 14, delete "of" and insert instead --off--.
Col. 3, line 39, delete "operable" and insert instead --operably--.
Col. 8, line 21, delete "sid" and insert instead --said--.

Signed and Sealed this

Fifth Day of April, 1994

Attest:

BRUCE LEHMAN

*Attesting Officer*   Commissioner of Patents and Trademarks